United States Patent
Ruprecht et al.

(10) Patent No.: US 11,684,666 B2
(45) Date of Patent: Jun. 27, 2023

(54) RECOMBINANT HIV COMPOSITIONS AND USES THEREOF IN ANIMAL MODELS

(71) Applicant: The University of Louisiana at Lafayette, Lafayette, LA (US)

(72) Inventors: Ruth M. Ruprecht, San Antonio, TX (US); Samir K. Lakhashe, San Antonio, TX (US)

(73) Assignee: University of Louisiana at Lafayette, Lafayette, LA (US)

(*) Notice: Subject to any disclaimer, the term of this patent is extended or adjusted under 35 U.S.C. 154(b) by 994 days.

(21) Appl. No.: 16/348,104

(22) PCT Filed: Nov. 7, 2017

(86) PCT No.: PCT/US2017/060398
§ 371 (c)(1),
(2) Date: May 7, 2019

(87) PCT Pub. No.: WO2018/085834
PCT Pub. Date: May 11, 2018

(65) Prior Publication Data
US 2020/0093916 A1 Mar. 26, 2020

Related U.S. Application Data

(60) Provisional application No. 62/418,661, filed on Nov. 7, 2016.

(51) Int. Cl.
| | |
|---|---|
| *A61K 39/00* | (2006.01) |
| *A61K 39/21* | (2006.01) |
| *A61K 39/12* | (2006.01) |
| *C07K 14/005* | (2006.01) |
| *C12N 15/11* | (2006.01) |
| *A01K 67/027* | (2006.01) |
| *C12N 7/00* | (2006.01) |

(52) U.S. Cl.
CPC ............ *A61K 39/21* (2013.01); *A01K 67/027* (2013.01); *C12N 7/00* (2013.01); *A01K 2207/10* (2013.01); *A01K 2207/20* (2013.01); *A01K 2227/106* (2013.01); *A01K 2267/0337* (2013.01); *C07K 2319/40* (2013.01); *C12N 2740/15022* (2013.01); *C12N 2740/16021* (2013.01); *C12N 2740/16122* (2013.01)

(58) Field of Classification Search
CPC .... A61K 39/12; A61K 39/21; A61K 2039/53; C07K 14/005; C12N 2740/16034
See application file for complete search history.

(56) References Cited

U.S. PATENT DOCUMENTS

| | | | | |
|---|---|---|---|---|
| 5,654,195 | A | * 8/1997 | Sodroski | ............. C12N 15/86 435/235.1 |
| 2010/0092513 | A1 | * 4/2010 | Ruprecht | ............ C07K 14/005 435/235.1 |

OTHER PUBLICATIONS

Mandl et al., "Divergent TLR7 and TLR9 signaling and type I interferon production distinguish pathogenic and nonpathogenic AIDS virus infections", Nature Medicine, 2008, 14(10):1077-1087.*
Barry et al., "Depletion of CD8+ cells in sooty mangabey monkeys naturally infected with simian immunodeficiency virus reveals limited role for immune control of virus replication in a natural host species", The Journal of Immunology, 2007:8002-8012.*
International Search Report and Written Opinion for PCT/US17/60398, dated Feb. 15, 2018.
Mandl et al. "Divergent TLR7 and TLR9 signaling and type i interferon production distinguish pathogenic and nonpathogenic AIDS virus infections" Nature medicine 14.10 (2008): 1077-1087.
Barry et al. "Depletion of CD8+ cells in sooty mangabey monkeys naturally infected with simian immunodeficiency virus reveals limited role for immune control of virus replication in a natural host species." The Journal of immunology 178.12 (2007): 8002-8012.

* cited by examiner

*Primary Examiner* — Barry A Chestnut
(74) *Attorney, Agent, or Firm* — Kean Miller LLP; Lauren J. Rucinski; Brian J. Servé

(57) ABSTRACT

Provided here are certain recombinant HIV compositions and animal models to evaluate prophylactic and therapeutic antiviral compositions.

11 Claims, 11 Drawing Sheets
Specification includes a Sequence Listing.

Original Nucleotide sequence of stHIV-C8457.3 molecular clone (10,119 nucleotides):

```
TGGATGGGTTAATTTACTCCAAGAAAAGGCAAGACATCCTTGATCTGTGGATCTATCACACA
CAAGGCTTCTTCCCTGATTGGCAAAACTACACACCGGGACCAGGGGACAGATATCCACTG
ACCTTTGGATGGTGCTTCAAGCTAGTGCCAGTTGACCCAAGAGAAGTAGAAGAAGCCACT
GAAGGAGAGAACAGCTGTTTACTACACCCTATGAGCCTGCATGGACTGGAAGATGCGGAC
AGAGAAGTATTAAGGTGGAAGTTTGACAGTCACCTAGCACACAGACACCTGGCCCGCGAG
CTACATCCGGAGTTTTACAAAGACTGCTGACACAGAAGGGACTTTCCGCTGGGACTTTCCA
CTGGGGCGTTCCAGGAGGTGTGGTCTGGGCGGGACTGGGGAGTGGCCAGCCCTCAGAT
GCTGCATATAAGCAGCTGCTTTTCGCTTGTACTGGGTCTCTCTAGGTAGACCAGATCTGAG
CCCGGGAGCTCTCTGGCTATCTAGGGAACCCACTGCTTAAGCCTCAATAAAGCTTGCCTTG
AGTGCTCTAAGTAGTGTGTGCCCGTCTGTTGTGTGACTCTGGTAACTAGAGATCCCTCAGA
CCCGTTGTGGTAGTGTGGAAAATCTCTAGCAGTGGCGCCCGAACAGGGACTTGAAAGCGA
AAGTAAGACCAGAGGAGATCTCTCGACGCAGGACTCGGCTTGCTGAAGTGCACTCGGCAA
GAGGCGAGAGCGGCGGCTGGTGAGTACGCCAATTTTATTTGACTAGCGGAGGCTAGGA
GGAGAGAGATGGGTGCGAGAGCGTCAATATTAAGAGGGGAAAAATTAGATAAGTGGGAAA
AAATTAGGTTAAGGCCAGGGGGAAAGAAACATTATATGCTAAAACACTTAGTATGGGCAAG
CAGGGAGCTGGAAAGATTTGCACTTAACCCTGGCCTTTTAGAGACATCAGAAGGCTGTAAA
CAAATAATGAAACAGCTACAACCAGCTCTTCAGACAGGAACAGAGGAACTTAGATCATTATA
TAACACAGTAGCAACTCTCTGTTGTGTACATGAAAAGATAGAGGTACGAGACACCAAGGAA
GCCTTAGACAAAATGGAAGAAGAACAAAACAAAGTCAGCAAAAAACACAGCAAGCAGAAG
CGGCTGACAAAGGAAAGGTCAGTCAAAACTATCCTATAGTGCAGAATCTCCAAGGGCAAAT
GGTACACCAGGCCATATCACCGAGAACTCTGAATGCATGGGTAAAAGTAATAGAGGAGAA
GGCTTTCAGCCCAGAGGTAATACCCATGTTTACAGCATTATCAGAAGGAGCCACCCCACAA
GATTTAAACACCATGTTAAATACAGTGGGGGGACATCAAGCAGCCATGCAAATGTTAAAAG
ATACCATTAATGAGGAGGCTGCAGAATGGGATAGGTTACATCCAGTGCATGCAGGGCCTAT
TGCACCAGGCCAAATAAGAGAACCAAGGGGAAGTGACATAGCAGGAACTACTAGTACCCT
TCAGGAGCAAATAGCATGGATGACAAATAACCCACCTATTCCAGTAGGAGACATCTATAAA
AGATGGATAATTCTGGGGTTAAATAAAATAGTAAGAATGTATAGCCCTGTCAGCATTTTGGA
CATAAAACAAGGACCAAAAGAACCCTTTAGAGACTATGTAGACAGGTTCTTTAAAACTTTAA
GAGCTGAACAGTCTACACAAGAGGTAAAAAACTGGATGACAGACACCTTGTTGGTCCAAAA
TGCGAACCCAGATTGTAAGACCATTTTAAGAGCATTAGGAACAGGGGCTACATTAGAAGAG
ATGATGACAGCATGTCAGGGAGTGGGGGGACCTAGCCACAAAGCAAGAGTTTTGGCTGAG
GCAATGAGCCAAGCAGGCAATACAAATATAATGATGCAGAGAAGCAATTTTAAAGGCCCTA
GAAGAATTATTAAATGTTTCAACTGTGGCAAGGAGGGGCACATAGCTAGAAATTGCAGGGC
CCCCAGGAAAAAGGGCTGTTGGAAATGTGGAAAGGAAGGACACCAAATAAAAGATTGTACT
GAGAGGCAGGCTAATTTTTTAGGGAAAATTTGGCCTTCCCACAAGGGAAGGCCAGGGAAT
TTCCTTCAGAACAGACCAGAGCCAACAGCCCCACCAGCAGAGAGTTTCAGGTTCGAGGAG
ACAACCCCCGCTCCGAAGCAGGAGCCGAACGACAGGGAACCCTTAACTTCCCTCAAATCA
CTCTTTGGCAGCGACCCCTCGTCTCAATAAAGTAGGGGGCCAAATAAGGGAGGCTCTCT
TAGATACAGGAGCAGATGATACAGTATTAGAAGACATAAATTTGCCAGGAAAATGGAAACC
AAAAATGATAGGAGGAATTGGAGGTTTTATCAAAGTAAGACAGTATGAACAAATACTTATAG
AAATTTGTGGAAAAAGGCTATAGGTACAGTATTAGTAGGACCTACCCCTGTCAACATAATT
GGAAGGAATATGTTGACACAGCTTGGGTGTACACTAAATTTTCCAATTAGTCCCATTGAAAC
```

FIG. 1D

```
TGTACCAGTAAAATTAAAGCCAGGGATGGATGGCCCAAGGGTTAAACAATGGCCATTGACA
GAAGAGAAAATAAAAGCATTAACAGCAATTTGTGAAGACATGGAGAAGGAAGGAAAAATTA
CAAAAATTGGGCCTGAAAATCCATATAACACTCCAGTATTTGCCATAAAAAAGAAGGACAGT
ACTAAGTGGAGAAAATTAGTAGATTTCAGGGAACTCAATAAAAGAACTCAAGACTTTTGGA
AGTTCAATTAGGAATACCACACCCAGCAGGGTTAAAAAAGAAAAAATCAGTGACAGTGCTG
GATGTGGGGGATGCATATTTTTCAGTTCCTTTAGATGAAAACTTCAGGAAATATACTGCATT
CACCATACCTAGTATAAACAATGCAGCACCAGGGATTAGATATCAATATAATGTGCTTCCAC
AGGGATGGAAAGGATCACCAGCAATATTCCAGAGTAGCATGACAAAAATCTTAGAGCCCTT
TAGGACACAAAATCCAGACATAGTTATCTATCAATATATGGATGACTTGTATGTAGGATCTG
ACTTGGAAATAGGGCAACATAGAGCAAAATAGAGAAGTTAAGAGAACATTTATTGAAATG
GGGACTCACCACACCAGACAAGAAACATCAGAAAGAACCCCATTTCTTTGGATGGGGTAT
GAACTCCATCCTGACAAATGGACAGTACAGCCTATACAGCTGCCAGAAAAGGATAGCTGGA
CTGTCAATGATATACAGAAGTTAGTGGGAAAATTAAACTGGGCAAGTCAGATTTACCCAGG
GATTAAAGTAAAGCAACTGTGTAAACTCCTTAGGGGAGCCAAAGCATTAACAGACATAGTA
CCACTGACTGAAGAAGCAGAATTAGAATTGGCAGAAAACAGGGAAATTTTAAAAGAACCAG
TACATGGAGTATATTATGACCCATCAAAAGACTTAATAGCTGAAATACAGAAACAGGGGTAT
GGCCAATGGACATACCAAATTTACCAAGAACCATTCAAAAATCTGAAAACAGGGAAGTATG
CAAAAATGAGGACTGCCCACACTAATGATGTAAAACAGTTAACAGAGGCAGTGCAAAAAAT
AGCCCTGGAAAGCATAGTAATATGGGGAAAGACTCCTAAATTTAGACTACCCATCCAAAAA
GACACATGGGAGGCATGGTGGACAGAATATTGGCAAGCCACCTGGATTCCTGAATGGGAG
TTTGTTAATACCCCTCCTCTAGTAAAATTATGGTACCAGCTGGAGAAAGAACCAATAATAGG
AGCAGAAACTTTCTATGTAGATGGAGCAGCTAATAGGGAAACTAAAGCAGGAAAGGCAGG
GTATGTTACTGACAAAGGAAGGCAGAAAATCGTTTCTCTAACTGAAACAACAAATCAGAAG
GCTGAACTACAAGCAGTTCAGCTAGCTTTGCAGGATTCAGGATTAGAAGTAAACATAGTAA
CAGACTCACAGTATGCCTTAGGAATTATTCAAGCACAACCAGATAAGAGTGAATCAGAATTA
GTCGCTCAGATAATAGAGCAGTTAATAAAAAAGGAAAGGGTCTACCTGTCATGGGTACCAG
CACATAAAGGAATTGGAGGAAATGAACAAGTAGATAAATTAGTCAGCAGTGGAATAAGGAA
AGTGCTGTTTCTAGATGGAATAGATAAGGCTCAAGAAGACCATGAAAAATATCACAGCAATT
GGAGAGCAATGGCTAATGAGTTTAATCTGCCACCCATAGTAGCAAAAGAAATAGTAGCTAG
CTGTGATAAATGTCAACTAAAAGGGGAAGCCATACATGGACAAGTAGACTGTAGTCCAGGG
ATCTGGCAATTAGATTGTACACATTTAGAAGGAAAAATCATCCTGGTAGCAGTCCATGTAGC
CAGTGGCTACATAGAAGCAGAGGTTATCCCAGCAGAAACAGGACAAGAAACAGCATACTA
CATACTAAAATTAGCAGGAAGATGGCCAGTAAAGGTAATACATACAGATAATGGCAGTAATT
TCACCAGTGCTGCAGTTAAGGCAGCCTGTTGGTGGGCAGGTATCCAACAGGAATTTGGAA
TCCCCTACAATCCCCAAAGTCAGGGAGTAGTAGAATCCATGAATAAAGAATTAAAGAAAATC
ATAGGGCAGGTAAGAGATCAAGCTGAGCACCTTAAGACAGCAGTACAAATGGCAGTATTCA
TTCACAATTTTAAAAGAAAGGGGGGATTGGGGGGTACAGTGCAGGGGAGAGAATAATAG
ACATAATAGCAACAGACATACAAACTAAAGAATTACAAAACCAAATTTTAAAAATTCGAAATT
TTCGGGTTTATTACAGAGACAGCAGAGACCCTATTTGGAAAGGACCAGCCAAACTACTCTG
GAAAGGTGAAGGGGCAGTAGTAATACAAGATAATAGTGACATAAAGGTAGTACCAAGGAG
GAAAGTAAAAATCATTAAGGACTACGGAAAACAGATGGCAGGTGCTGATTGTGTGGCAGGT
AGACAGGACGAGGATTAGACCGCGGTTATGGAGGAGGAAAAGAGGTGGATAGCAGTTCC
CACATGGAGGATACCGGAGAGGCTAGAGAGGTGGCATAGCCTCATAAAATATCTGAAATAT
AAAACTAAAGATCTACAAAAGGTTTGCTATGTGCCCCATTTTAAGGTCGGATGGGCATGGT
```

FIG. 1D CON'T

```
GGACCTGCAGCAGAGTAATCTTCCCACTACAGGAAGGAAGCCATTTAGAAGTACAAGGGT
ATTGGCATTTGACACCAGAAAAGGGTGGCTCAGTACTTATGCAGTGAGGATAACCTGGTA
CTCAAAGAACTTTTGGACAGATGTAACACCAAACTATGCAGACATTTTACTGCATAGCACTT
ATTTCCCTTGCTTTACAGCGGGAGAAGTGAGAAGGGCCATCAGGGGAGAACAACTGCTGT
CTTGCTGCAGGTTCCCGAGAGCTCATAAGTACCAGGTACCAAGCCTACAGTACTTAGCACT
GAAAGTAGTAAGCGATGTCAGATCCCAGGGAGAGAATCCCACCTGGAAACAGTGGAGAAG
AGACAATAGGAGAGGCCTTCGAATGGCTAAACAGAACAGTAGAGGAGATAAACAGAGAGG
CGGTAAACCACCTACCAAGGGAGCTAATTTTCCAGGTTTGGCAAAGGTCTTGGGAATACTG
GCATGATGAACAAGGGATGTCACCAAGCTATGTAAAATACAGATACTTGTGTTTAATACAAA
AGGCTTTATTTATGCATTGCAAGAAAGGCTGTAGATGTCTAGGGGAAGGACATGGGGCAG
GGGGATGGAGACCAGGACCTCCTCCTCCTCCCCCTCCAGGACTAGCATAAATGGAAGAAA
GACCTCCAGAAAATGAAGGACCACAAAGGGAACCATGGGATGAATGGGTAGTGGAGGTTC
TGGAAGAACTGAAAGAAGAAGCTTTAAAACATTTTGATCCTCGCTTGCTAACTGCACTTGGT
AATCATATCTATAATCGTCACGGAGACACTCTAGAGGGAGCAGGAGAACTCATTAGAATCC
TCCAACGAGCGCTCTTCATGCATTTCAGAGGCGGATGCATCCACTCCAGAATCGGCCAAC
CTGGGGGAGGAAATCCTCTCTCAGCTATACCGCCCTCTAGAAGCATGCGCATGCTGTAGA
GCAAGAAATGGAGCCAGTAGATCCTAGACTAGAGCCCTGGAAGCATCCAGGAAGCAGGCC
TAAAACTGCTTGTACCAATTGCTATTGTAAAAGTGTTGCTTTCATTGCCAAGTTTGTTTCAT
AACAAAAGCCCTAGGCATCTCCTATGGCAGGAAGAAGCGGAGACAGCGACGAAGAGCTCA
TCAGAACAGTCAGACTCATCAAGCTTCTCTATCAAAGCAGTAAGTAGTACATGTAATGCAAT
CTATACAAATAGAAATAGTAGCATTAGTAGTAGCAATAATAATAGCAATAGTTGTGTGGTCC
ATAGTAATCATAGAATATAGGAAAATATTAAGACAAAGAAAAATAGACAGGTTAATTAATAGA
CTAATAGAAAGAGCAGAAGACAGTGGCAATGAGAGTGAAGGAGAAATATCAGCACTTGTG
GAGATGGGGGTGGAGATGGGGCATCATGCTCCTTGGGATGTTGATGATCTGTAGTGCTAC
AGAAAAATTGTGGGTCACAGTCTATTATGGGGTACCTGTATGGAAAGAAGCAAAAACTACT
TTATTCTGTGCATCAAATGCTAAAGCATATGAGAAGAAGTACATAACATCTGGGCTACACA
TGCCTGTGTACCCACAGACCCCAACCCACAAGAAATAGTTTTGGGAAATGTAACAGAAAAT
TTTAACATGTGGAAAAATGACATGGTGGATCAGATGCATGAGGATATAATCAGTTTATGGGA
TCAAAGCCTAAAGCCATGTGTAAAGTTGACTTCACTCTGTGTCACTTTAAAGTGTAGTAATT
TTACCGGGAAGAGTAATGTTACCTACAAAGGGGATATGGAAGTAAAAAATTGCTCTTTCAAT
GTAACCACAGAAATAAGAGATAAGAAGCAGAAAGTGTATGCTCTTTTTTATAGACTTGATAT
AACACCACTTGATGACAACTCTAGTGAGTATATATTAATAAATTGCAATTCCTCAACCATAAC
ACAAGCCTGTCCAAAGGTCAATTTTGACCCAATTCCTATACATTATTGTGCTCCAGCTGGTT
ATGCGATTCTAAAGTGTAATAATAAGACATTTAATGGGACAGGACCATGCCATAATGTCAGT
ACAGTACAATGTACACATGGAATTAAGCCAGTGGTATCAACTCAACTACTGTTAAACGGTAG
CCTAGCAGAAGGGGAGATAATAATTAGATCTGAAAATCTGACAGACAATGTCAAAACAATAA
TAGTACACTTTAATGAATCTGTAGAAATTACTTGTACAAGACCCAACAATAATACAAGAAAAA
GTATAAGCATAGGACCAGGACAAGCAATCTATGCCACAGGTGATATAATAGGAGACATAAG
ACAAGCACACTGTAACATTAGTAAAGAAAATTGGAACAAAACTTTACAATGGGTAAGGGGA
AAATTAAAAGAACACTTCCCTAATAAAACAATAGTATTTAAACCATCCTCAGGAGGGGATCT
AGAAATTACAACACATAGCTTTAATTGTAGAGGAGAATTTTTCTATTGCAACACATCAAAACT
GTTTAATAGTACAGACAATAGTACACACATGGGTACAGAAAATAATACAATCATCACAATCC
CATGTAGAATAAAACAAATTATAAACATGTGGCAGGAGGTAGGACGAGCAATGTATGCCCC
CCCCATAGAAGGAAACATAACATGTAAATCAAATATCACAGGACTACTACTGGTACGTGAT
```

FIG. 1D CON'T

```
GGAGGATGGGACAACAGTACAAATGACACAGAAACATTCAGGCCTGGAGGAGGAGATATG
AGGGACAATTGGAGAAGTGAATTATATAAATATAAGGTGGTAGAAGTCAAGCCATTGGGAA
TAGCACCCACTAAGGCAAAAGGAGAGTGGTGGAGAGAGAAAAAGAGCAGTGGGAATAG
GAGCTGTGTTCCTTGGGTTCTTGGGAGCAGCAGGAAGCACTATGGGCGCGGCGTCAATAA
CGCTGACGGTACAGGCCAGACAACTGTTGTCTGGTATAGTGCAGCAGCAAGACAATTTGC
TGAGAGCTATAGAGGCGCAACAACATATGTTGCAACTCACAGTCTGGGGCATTAAGCAGCT
CCAGGCGAGAGTCCTGGCTATAGAAAGATACCTACAGGATCAACAGCTCCTAGGGATTTG
GGGCTGCTCTGGAAAACTCATCTGCACCACTGCTGTGCCTTGGAACGACAGTTGGAGTAA
TAAATCTCAAACAGATATTTGGGAGAACATGACCTGGATGCAGTGGGATAGAGAAATTAGT
AGACACACAGACACAATATACAGGTTGCTTGAAGACTCACAAAACCAGCAGGAGAAAAATG
AAAAAGATTTATTAGCATTGGACAGTTGGAAAAATTTGTGGAATTGGTTTAGCATAACAAGG
TGGCTGTGGTATATAAAAATATTCATAATGATAGTAGGAGGCCTGATAGGTTTGAGAATAAT
TTTTGCTGTGCTCTCGATAGTGAATAGAGTTAGGCAGGGATACTCACCATTATCGTTTCAGA
CCCACCTCCCACTTCCGAGGGGAGCCGACAGGCCCGAAGGAATAGAAGAAGAAGGTGGA
GAGAGAGACAGAGACAGATCCATTCGATTAGTGACCGGATCCTTAGCACTTATCTGGGAC
GATCTGCGGAGCCTGTGCCTCTTCAGCTACCACCGCTTGAGAGACTTACTCTTGATTGTAA
CGAGGACTGTGGAACTCCTGGGACGCAGAGGGTGGGAAGCCCTCAAATATTGGTGGAATC
TCCTACTGTATTGGAGTCAGGAACTAAAGAATAGTGCTGTTAGCTTGCTCAACGCCACAGC
CATAGCAGTAAGACAATACGGGTGGAGCTATTTCCACGAGGCGGTCCAGGCCGTCTGGAG
ATCTGCGACAGAGACTCTTGCGGGCGCGTGGGGAGACTTATGGGAGATTCTTAGGAGAGG
TGGAAGATGGATACTCGCAATCCCCAGGAGGATTAGACAAGGGCTCGAGCTCACTCTCTT
GTGAGCGATCGCATGGGGGGCAAGTGGTCAAAAGCAGTATAGTTGGATGGCCTGCTGTA
AGAGAAAGAATAAGACAAACTGCTCCAGCAGCAACAGGAGTAGGAGCAGCGTCTCAAGAC
TTAGATACACATGGGGCACTTACAACCAGCAACACAGTTAGCAACAATGCTGATTGTGCCT
GGTTGGAAGCACAAGAGGAGAAAGACGAGGTAGGCTTTCCAGTCAGACCTCAGGTACCTT
TAAGACCAATGACTTATAAGGCAGCATTCGATCTCAGCTTCTTTTTAAAAGAAAAGGGGGG
ACTGGATGGGTTAATTTACTCCAAGAAAAGGCAAGACATCCTTGATCTGTGGATCTATCACA
CACAAGGCTTCTTCCCTGATTGGCAAAACTACACACCGGGACCAGGGGTCAGATATCCACT
GACCTTTGGATGGTGCTTCAAGCTAGTGCCAGTTGACCCAAGGGAAGTAGAAGAAGCCAC
TGAAGGAGAGAACAGCTGTTTACTACACCCTATGAGCCTGCATGGACTGGAAGATGCGGA
CAGAGAAGTATTAAGGTGGAAGTTTGACAGTCACCTAGCGCACAGACACATGGCCCGCGA
GCTACATCCGGAGTTTTACAAAGACTGCTGACACAGAAGGGACTTTCCGCTGGGACTTTCC
ACTGGGGCGTTCCAGGAGGTGTGGTCTGGGCGGGACTGGGGAGTGGCCAGCCCTCAGAT
GCTGCATATAAGCAGCTGCTTTTCGCTTGTACTGGGTCTCTCTAGGTAGACCAGATCTGAG
CCCGGGAGCTCTCTGGCTATCTAGGGAACCCACTGCTTAAGCCTCAATAAAGCTTGCCTTG
AGTGCTCTAAGTAGTGTGTGCCCGTCTGTTGTGTGACTCTGGTAACTAGAGATCCCTCAGA
CCC
```

FIG. 1D CON'T

RECOMBINANT HIV COMPOSITIONS AND USES THEREOF IN ANIMAL MODELS

GOVERNMENT SUPPORT

This invention was made with government support under Grant Nos. P01 AI 048240 (ARRA Supplement for Cores A and B), R56 AI104430, and R01 AI18586 awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Oct. 31, 2019, is named 0074714_000105-US-_SL.txt and is 13,717 bytes in size.

TECHNICAL FIELD

The present disclosure relates to certain recombinant HIV compositions and animal models to evaluate prophylactic and therapeutic antiviral compositions, more specifically to recombinant HIV compositions and animal models directed to specific HIV subtypes, such as HIV-1 clade C.

BACKGROUND

Animal models in which the efficacy of immunogens based on various genes of HIV-1 (env, gag, tat, net) can be evaluated would be an important tool to advance HIV/AIDS vaccine research. However, such a tool is not available since HIV-1 can infect only humans and chimpanzees. Testing the efficacy of HIV-1 vaccine candidates in human clinical trials is challenging as thousands of volunteers are needed (the RV144 trial enrolled 16,400 volunteers). Therefore, development of a suitable new animal model for preclinical testing of HIV-1 vaccines as well as antiviral compositions, such as small molecules and biologics against HIV infections, is very important.

SUMMARY

Disclosed herein are animal models and methods of addressing the shortcomings of the art, and may provide any number of additional or alternative advantages.

Embodiments of the invention include methods for developing a human immunodeficiency virus (HIV) infection in a non-human primate. An exemplary method providing a non-human primate with weakened immune response, the weakened immune response being result of administration of IFN type 1 receptor antagonist to the non-human primate; and exposing the non-human primate to a chimeric HIV composition containing sequences from a human immunodeficiency virus genome of subtype clade C. The non-human primate can be a pig-tailed macaque. Furthermore, the weakened immune response can be the result of depletion of CD8$^+$ cells in the non-human primate. The weakened immune response can be the result of depletion of B cells in the non-human primate.

Embodiments of the invention also include chimeric HIV compositions. An exemplary composition contains sequences from a human immunodeficiency virus genome of subtype clade C, and nucleotide sequences from the HIV1084i and SIVmac239 vif constructs.

Embodiments of the invention include methods for evaluating an anti-HIV compound in a non-human primate. An exemplary method includes providing a non-human primate with weakened immune response, the weakened immune response being result of administration of IFN type 1 receptor antagonist to the non-human primate; exposing the non-human primate to a chimeric HIV composition containing sequences from a human immunodeficiency virus genome of subtype clade C to obtain an exposed non-human primate; administering an anti-HIV compound to the exposed non-human primate; and monitoring the exposed non-human primate for changes in immune cells of the exposed non-human primate in response to the anti-HIV compound. The non-human primate can be a pig-tailed macaque. Furthermore, the weakened immune response can be the result of depletion of CD8$^+$ cells in the non-human primate. The weakened immune response can be the result of depletion of B cells in the non-human primate.

Embodiments of the invention include methods for evaluating a HIV vaccine in a non-human primate. An exemplary method includes providing a non-human primate with weakened immune response, the weakened immune response being result of administration of IFN type 1 receptor antagonist to the non-human primate; exposing the non-human primate to a chimeric HIV composition containing sequences from a human immunodeficiency virus genome of subtype clade C to obtain an exposed non-human primate; administering a HIV vaccine to the exposed non-human primate; and monitoring the exposed non-human primate for changes in immune cells of the exposed non-human primate in response to the HIV vaccine. The non-human primate can be a pig-tailed macaque. Furthermore, the weakened immune response can be the result of depletion of CD8$^+$ cells in the non-human primate. The weakened immune response can be the result of depletion of B cells in the non-human primate.

Numerous other aspects, features and benefits of the present disclosure may be made apparent from the following detailed description taken together with the drawing figures. The pharmaceutical compositions can include compounds described herein, other components, or ingredients depending on desired prevention and treatment goals. It should be further understood that both the foregoing general description and the following detailed description are exemplary and explanatory and are intended to provide further explanation of the invention as claimed.

BRIEF DESCRIPTION OF THE DRAWINGS

The present disclosure can be better understood by referring to the following figures. These figures also illustrate several aspects of the disclosure.

Figure 1:
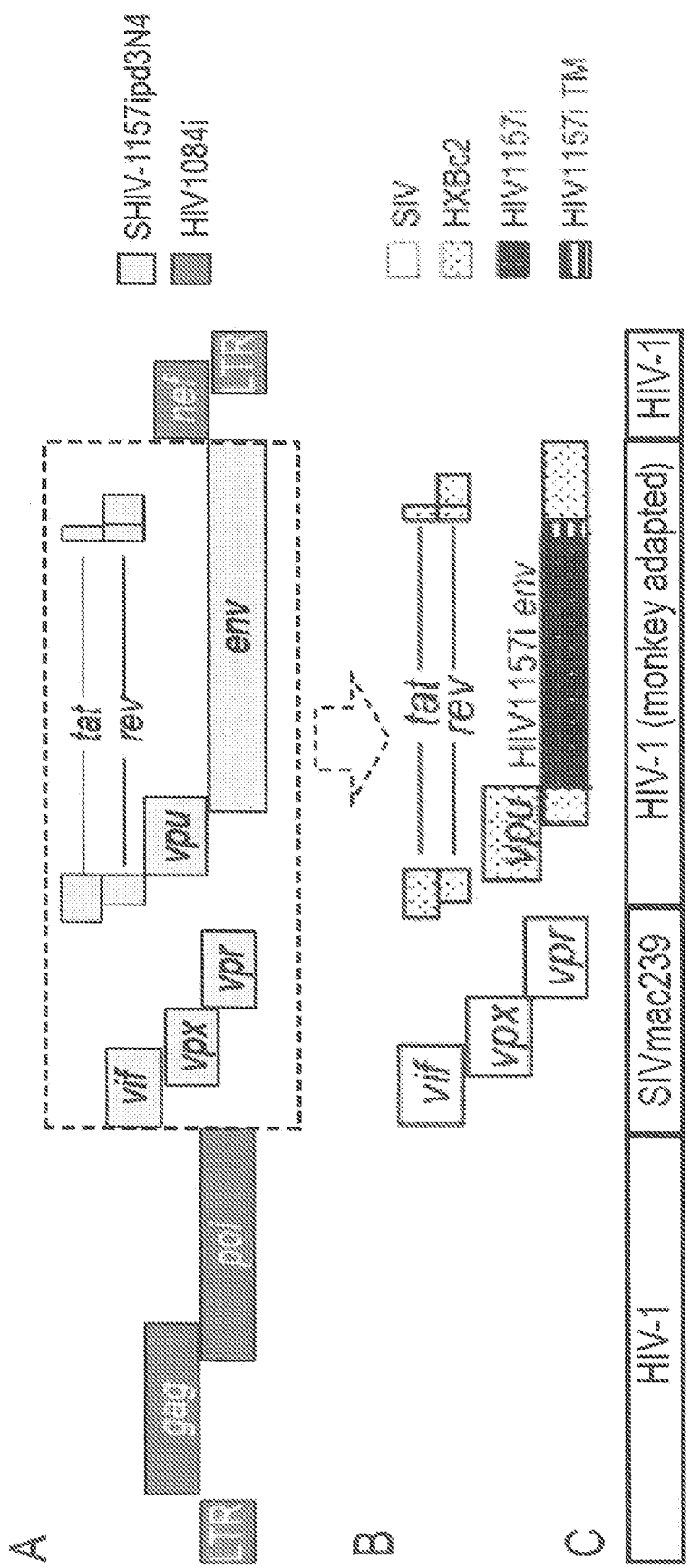
FIGS. 1A-1C provide a schematic representation of construction of the simian-tropic HIV-C chimeric virus, according to an exemplary embodiment.
FIG. 1D is the nucleotide sequence of the stHIV-C8457.3 molecular clone (SEQ ID NO: 1).

FIG. 5 is a graphical representation of the expression of the p24 protein to monitor the replication of stHIV chimeric viruses in cultured peripheral blood mononuclear cells of two naive pig-tailed macaques with or without depletion of $CD8^+$ cells.

FIG. 6 is a graphical representation of the genome sequence analysis of the ex vivo adapted stHIV-C8457, according to an exemplary embodiment.

FIGS. 7A and 7B are graphical representations of the viral level in the blood for two PMs for extended periods of time and even in the presence of CD8+ cells, according to an exemplary embodiment.

DETAILED DESCRIPTION

Reference will now be made to the exemplary embodiments illustrated in the drawings, and specific language will be used here to describe the same. It will nevertheless be understood that no limitation of the scope of the invention is thereby intended. Alterations and further modifications of the inventive features illustrated here, and additional applications of the principles of the inventions as illustrated here, which would occur to one skilled in the relevant art and having possession of this disclosure, are to be considered within the scope of the invention.

As used here, the following terms may have the following definitions:

The term "HIV" is meant to include different form of the Human Immunodeficiency Virus, such as HIV-1 and HIV-2 and also the simian immunodeficiency virus (SIV). HIV-1 is organized into groups and subtypes (clades).

As used herein, "antigen" refers to a molecule containing one or more epitopes (either linear, conformational or both) that will stimulate a host's immune system to make a humoral and/or cellular antigen-specific response. The term is used interchangeably with the term "immunogen." As used herein, an "antibody" includes any reactive fragment or fragments of antibodies such as Fab molecules, Fab proteins, single chain polypeptides, or the multi-functional antibodies having binding affinity for an antigen. The term includes chimeric antibodies, altered antibodies, univalent antibodies, bi-specific antibodies, monoclonal antibodies, polyclonal antibodies, human antibodies and humanized antibodies. Methods for preparing antibodies are well known in the art and described herein. A "neutralizing antibody" is an antibody that prevents HIV infection of target cells. As used herein, the term "vaccine(s)" or "vaccine composition" means a recombinant nucleotide or peptide sequence, the administration of which is intended to elicit an immune response(s) that can prevent and/or lessen the severity of one or more infectious diseases. An "anti-HIV compound" means a composition that interacts with the HIV virus and is capable of inhibiting or blocking entry, replication, infectivity, or other activity of a HIV virus.

HIV-1 has very restricted host range and can infect only humans and chimpanzees. The use of chimpanzees raises many ethical issues and therefore for preclinical HIV/AIDS vaccine-related research, surrogate animal models are used. Most commonly, rhesus macaques (RMs) are immunized with vaccine candidates and are challenged with simian immunodeficiency virus (SW) or recombinant simian-human immunodeficiency virus (SHIV). Although HIV and SIV are closely related and cause AIDS in the susceptible host species, the genome sequences are significantly different. Therefore, in RM/SIV studies, RMs are vaccinated with immunogens that are based on the genome sequence of SIV and not HIV-1. Commonly used recombinant SHIVs (in vaccine-related research) have a genome that has the SIV backbone, but the vpu, tat, rev, and env genes are of HIV-1 origin. Therefore in RM/SHIV studies, the efficacy of HIV-1 env-based immunogens can be evaluated; but the immunogens based on other important gene targets (gag, tat, net) cannot be tested. Certain embodiments of the invention include animal models in which the efficacy of immunogens based on various genes of HIV-1 (env gag, tat, rev, nef) can be evaluated. The generation of primate lentiviruses based mostly upon HIV-1 and replication-competent in macaques would facilitate the development of treatment or prevention strategies with drugs and/or immunological approaches.

Chimeric nucleotide composition, such as stHIV-C-based constructs described here, are important tools for research programs aimed at prevention of infection with the world's most common genetic subtype. Prevention programs can involve testing of vaccines, drugs, monoclonal antibodies or microbicides—alone or in combination. Moreover, conducting human clinical trials can be complicated by the need to give standard of care treatment rather than placebo. Given the rapid increase of access to antiviral drugs (ARVs) in the world, clinical trials will need to compare ARV+/−vaccines (or other modalities). Given the high degree of efficacy of ARVs, clinical trials involving just vaccines may no longer be feasible. In this case, studies in non-human primate (NHP) models would be important in the evaluation and clinical development of vaccine candidates.

Certain embodiments include a viral composition containing the HIV-1 long terminal repeat (LTR) to better reflect HIV-1 biology in a non-human animal model as compared to SIV LTR. As HIV-1 is not restricted by the TRIM5α of pig-tailed macaques (PMs), this species is more permissive to HIV-1 than others. As most new HIV-1 infections are due to RS-tropic HIV-1 clade C (HIV-C), the ideal tool to test the efficacy of HIV-1 vaccine candidates would be an RS-tropic stHIV-C that can replicate and show disease progression in PMs. Provided herein are nucleotide constructs that comprise the progeny of simian-tropic HIV clade C (stHIV-C) adapted to pig-tailed macaques that can be used for preclinical testing of HIV-1 vaccines as well as drugs.

Embodiments of the invention include a stHIV-C chimera using an infectious molecular clone of a recently transmitted pediatric HIV-C, HIV1084i, and SIVmac239 vif. The HIV-C env gene was derived from the RS-tropic infectious molecular clone, SHIV-1157ipd3N4, a standard simian-human immunodeficiency virus built from the SIVmac239 backbone that had been adapted to rhesus monkeys and interestingly, SHIV-1157ipd3N4 replicated very well and caused AIDS in PMs without further adaptation. The HIV-C env gene was derived from a virus with pathogenic potential in PMs. The newly constructed stHIV-C chimera, stHIV-C8457, replicated ex vivo in some but not all peripheral blood mononuclear cells (PBMC) from different PM donors. To further adapt the stHIV-C8457 to the new species, it was inoculated into four PMs in a serial fashion.

In one aspect of the invention, to overcome the restriction imposed by host immune mechanisms, $CD8^+$ cells [the cytotoxic anti-CD8 mAb not only kills $CD8^+$ T cells, but also $CD8^+$ natural killer (NK) cells] and B cells were depleted from some animals at the time of virus inoculation. This immunodepletion was performed to ablate $CD8^+$ cell-mediated restriction of virus replication (due to soluble factors and virus-specific cytolytic activity) and to preclude the generation of virus-specific antibody responses.

In another aspect, further elimination of additional host suppression of stHIV-C was achieved by a novel approach. The CD8+ cell immunodepletion was combined with the administration of investigational interferon (IFN) type 1 receptor antagonist (IFN-1ant). As IFNs are the key molecules that induce IFN-stimulated genes and generate the "antiviral state", blocking the action of type 1 IFNs can further facilitate establishment or progression of the disease.

In another aspect, to block more host innate 1 adaptive immune responses, B cells can be depleted in addition to the combined use of an anti-CD8 mAb and the administration of IFN-1ant in an animal model. This approach provides potentially unrestricted viral replication (without selection pressure) leading to the emergence of several new mutant viruses. Therefore, after transfer of these quasispecies to the new immunocompetent host, better adapted virus can be selected.

In an aspect of the invention, stHIV-C reservoirs have been established in several PMs that are critical to evaluate strategies for HIV reservoir eradication. This NHP model is ideal, because the virus contains the real HIV-1 clade C LTR. PMs with chronic stHIV-C infection can also be used to study elimination of virus reservoirs by LTR activating drugs and/or other treatment modalities.

In recent years, many host restriction factors have been identified that inhibit the replication of HIV-1 in NHPs. These factors include: (I) TRIM5α, which targets HIV-1 capsid proteins and blocks early post-entry replication steps, (2) APOBEC3G (A3G), a cytidine deaminase that causes hypermutations, and (3) tetherin, which is induced by interferon-α (IFN-α) and inhibits the release of virions from infected cells. All these mechanisms are overcome by HIV-1 in human cells. The HIV-1 genetic material encodes a capsid protein which is resistant to human TRIM5α, vif that facilitates degradation of human A3G, and vpu that overcomes action of human tetherin. In NHPs, one or more of these mechanisms or additional mechanisms block HIV-1 replication. Among NHPs, the TRIM5 isoform of pig-tailed macaques does not inhibit HIV-1 replication. However, pig-tailed macaques carry an A3G that is not degraded by HIV-1 vif. Therefore, HIV-1 molecular clones were constructed in which the HIV-1 vif was replaced by the SIV vif, which can overcome A3G of pig-tailed macaques; the resulting HIV is termed simian-tropic HIV (stHIV). The early stHIV constructs were X4-tropic and did not cause persistent viremia in pig-tailed macaques. Recently, a new stHIV (based upon HIV$_{NL4-3}$, a clade B clone) carrying SIVmac vif and an RS-tropic envelope has been reported. But, most new HIV-1 infections are due to RS-tropic HIV-1 clade C. It is important to develop an HIV-1 clade C-based simian-tropic HIV (stHIV-C) that exhibits restricted CCR5 tropism. The ideal tool to test the efficacy of HIV-1 vaccine candidates is an RS-tropic stHIV-C that can replicate and show disease progression in the pig-tailed macaques without CD8+ cell depletion. The stHIV-C chimera, described here in an embodiment, contains an infectious molecular clone of a recently transmitted pediatric HIV-C, HIV1084i, and SIVmac239 vif. This resulting chimera, stHIV-C8457, replicated in pig-tailed macaques and also established virus reservoirs. The virus has undergone adaptation in pig-tailed macaques. An innovative approach has been proposed to obtain progeny of stHIV-C8457 that can resist early innate immune mechanisms and show improved replication fitness in pig-tailed macaques.

Innate host immune responses are ablated to facilitate enhanced stHIV-C replication in the pig-tailed macaques. The high mutation rate of HIV-1 coupled with high virus replication leads to emergence of diverse quasispecies. Variants with improved replication fitness can then be selected by reapplying the innate immune selection pressure. To ablate-innate host immune responses, a novel strategy was developed. Type 1 interferons are the key molecules that induce interferon-stimulated genes and generate the "antiviral state", so a novel antagonist was used to block the action of type 1 IFNs. The blockade of type 1 IFN signaling along with depletion of CD8+ cells was attempted to maximize stHIV-C replication. The newly generated viral quasispecies were inoculated into an immunocompetent PM. The stHIV-C progeny that has the best replication fitness among all variants was selected for further characterization.

Embodiments of the invention include tools and animal models for the preclinical testing of vaccine candidates against the world's most prevalent HIV-1 clade. As stHIV encodes the HIV-1 reverse transcriptase and protease, the efficacy of drugs targeting these enzymes can also be investigated in the stHIV model. Furthermore, the PM/stHIV model can also be used for evaluating HIV-1 therapeutic modalities.

Difference in outcomes to different chimeric constructs can attributed to immunological perturbations during early infection. Early innate immune responses play an important role in the control of viral replication; a virus that can overcome those early innate immune responses is needed for the advancement of PM/stHIV model. An existing PM/stHIV model is based on HIV-1 clade B and this virus caused disease progression only when CD8+ cells are depleted during acute phase of virus replication. The adapted virus also showed R5 to X4 switch in the co-receptor usage. Since the majority of new HIV-1 infections are clue to RS-tropic HIV-1 clade C, there is a great need for HIV-1 Blade C-based simian tropic HIV (stHIV-C) that has restricted CCR5 tropism. This ideal tool can be used to test efficacy of HIV-1 vaccine candidates as the R5 tropic stHIV-C that can replicate and show disease progression in the pig-tailed macaques without CD8+ T cell depletion.

An embodiment of the invention includes a stHIV-C chimera using infectious molecular clone of a recently transmitted pediatric HIV-C, HIV1084i (Grisson et al., 2004), and SIVmac239 vif (FIG. 1). The resulting chimera, stHIV-C8457 (also referred as stHIV-C), replicated in peripheral blood mononuclear cells (PBMC) of pig-tailed macaques and was infectious in vivo. The virus has undergone partial adaptation and appears to be controlled by the innate immune responses. Embodiments of the invention include derivatives of stHIV-C8457 that are resistant to early innate immune mechanisms.

Molecular Cloning of stHIV-C8457, Replication Competence, and Co-Receptor Usage

The stHIV-C8457 clone, as described in FIGS. 1A-1C, was made using HIV-C molecular clone HIV1084i, obtained from recently transmitted HIV-C isolate from Zambia.

Figure 2:
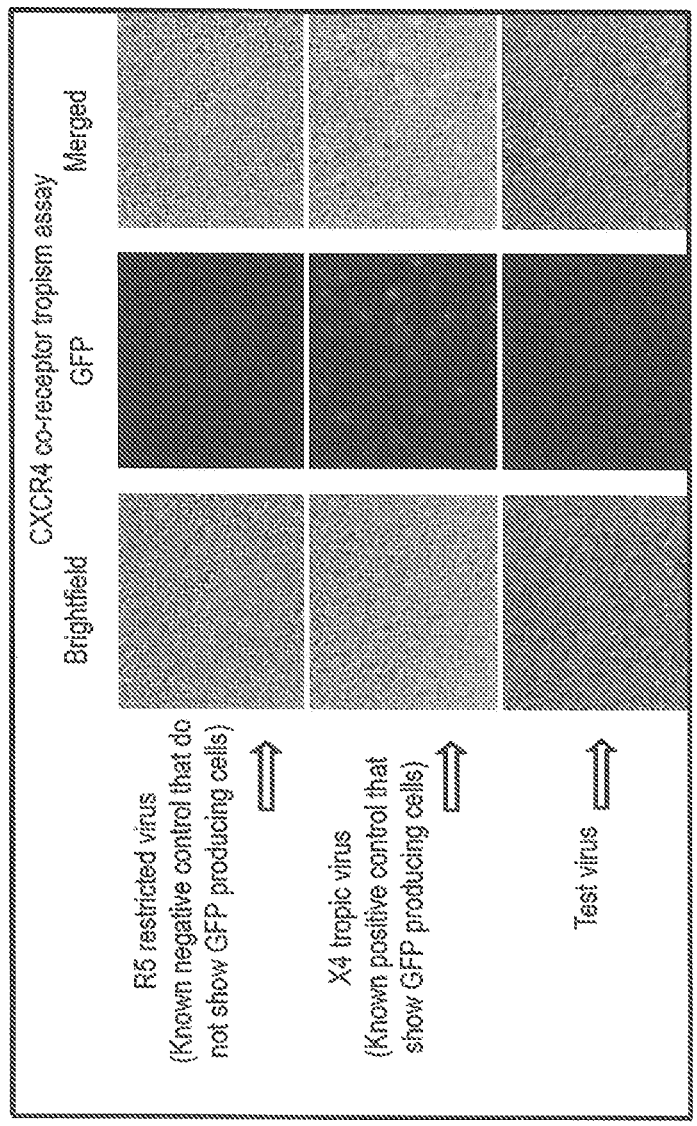
FIG. 2 is a set of CXCR4 co-receptor tropism assays to determine the co-receptor usage of the various chimeric viruses, according to an exemplary embodiment.

To obtain HIV-1 that is replication competent in the pig-tailed macaques, the vif gene of HIV1084i was replaced with that of SIVmac239. For this exchange, a segment from the start of vif to the end of env of HIV1084i was swapped with the corresponding region of SHIV-1157ipd3N4 (FIGS. 1A-1C). The latter (Song et al., 2006) is an R5 clade C SHIV (SHIV-C) that is known to cause a high level of acute viremia, depletion of CD4+ T cells in the mucosa, and has caused AIDS in pig-tailed macaques (Ho et al., 2009). The segment of SHIV-1157ipd3N4 contains: vif vpx, & vpr (derived from SIVmac239); tat, rev, & vpu (derived from HIV-1 HxB2); env (ectodomain derived from HIV1157i (another recently transmitted HIV-C isolate from Zambia) and parts of gp41 derived from HxB2). The resulting chimera is referred as stHIV-C8457 or stHIV-C. The sequence listing for this chimeric virus is provided as FIG. 1D. The parental stHIV-C (cell-free supernatant derived from transfected 293T cells) was also tested for coreceptor usage. A panel of U87.CD4 cells expressing CCR1, CCR2, CCR3, CXCR4, or CCR5, and also GHOST-Bob or GHOST-Bonzo was used for this experiment. The virus replicated only in the cell line that expressed CCR5. The parental stHIV-C8457 also did not produce any 'green' signals of infection in the CEMx174.GFP cells which express CXCR4 (FIG. 2). This shows exclusive R5 tropism of stHIV-C construct. The DNA of this molecular construct was transfected to 293T cells and supernatant containing viral particles was harvested. The presence of viral particles in the supernatant was confirmed by measuring HIV-1 p24 concentration. This virus stock was tested for 50% tissue culture infectivity dose ($TCID_{50}$) using TZM-b1 cells.

This virus stock was characterized for replication competency in the PBMC of six randomly selected pig-tailed macaques and two anonymous human donors. The virus (stHIV-C) was infectious and replication was similar to wild-type virus (HIV1084i) in the human PBMC. The virus also replicated in the PBMC obtained from three out of six pig-tailed macaques but not in all PBMC specimens. This indicated that further adaptation was needed for this virus in the new species.

Figure 3:
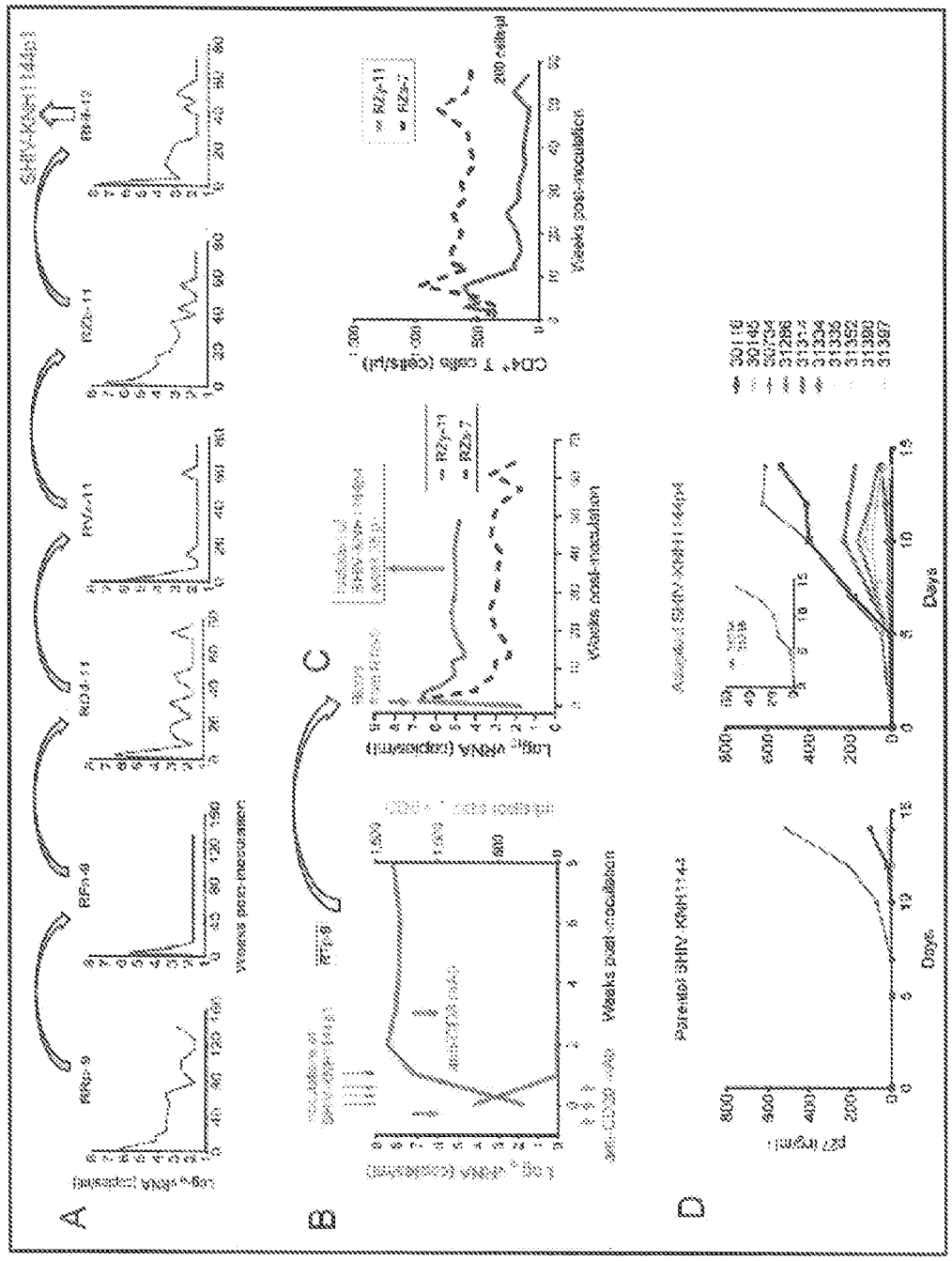
FIG. 3 is a graphical representation of the strategy employed to adapt a chimeric virus, a conventional simian-human immunodeficiency virus (SHIV), in rhesus monkeys, according to an exemplary embodiment, using depletion of immune system cells.

A novel adaptation strategy was deployed that has yielded recombinant SHIV-KNH1144p4 (clade A SHIV) (FIG. 3), SHIV-Bo159N4 (clade B SHIV), and SHIV-E (clade E SHIV) with better replication fitness in rhesus macaques compared to their parental forms. During initial adaptation of SHIV-KNH1144p4, rapid serial passage of virus was performed through six RMs; infected blood or reisolated virus was transferred from one infected animal to the next recipient (FIG. 3A). The virus was passaged from one RM to next at peak viremia of acute phase of infection to minimize the impact of adaptive immune responses on virus replication. However, this strategy was disappointing as replication kinetics of SHIV-KNH1144p4 after passage through six RMs was suboptimal and virus was suppressed in all six RMs during chronic phase of infection (FIG. 3A). A change in strategy helped maximize virus replication. In next RM, anti-CD8 antibodies (cM-T807) and the anti-CD20 antibodies (rituxirnab) were administered to deplete $CD8^+$ cells and B cells, respectively, at the time of virus inoculation. This immunodepletion was performed to ablate $CD8^+$ cell-mediated restriction of virus replication (due to soluble factors and virus-specific cytolytic activity) and to preclude the generation of virus-specific antibody responses. This immunodepletion can provide a chance of unrestricted viral replication (without selection pressure) leading to the emergence of several new mutant viruses. After transfer of these quasispecies to the new immunocompetent host, better adapted virus can be selected. The immunodepleted animal showed sustained high viral loads ($>10^7$ copies/ml for several weeks) (FIG. 3B). Next, whole blood was transferred blood from highly viremic, immunodepleted RM to two naive immunocompetent macaques. The fact that both of these RMs demonstrated high peaks of viral RNA (vRNA), steady-state viremia, and depletion of absolute numbers of $CD4^+$ T cells confirmed the emergence of well adapted virus (FIG. 3C). The replication of adapted SHIV-KNH1144p4 in PBMCs of ten randomly selected RMs was significantly improved compared to parental virus (before adaptation) (FIG. 3D).

Figure 4:
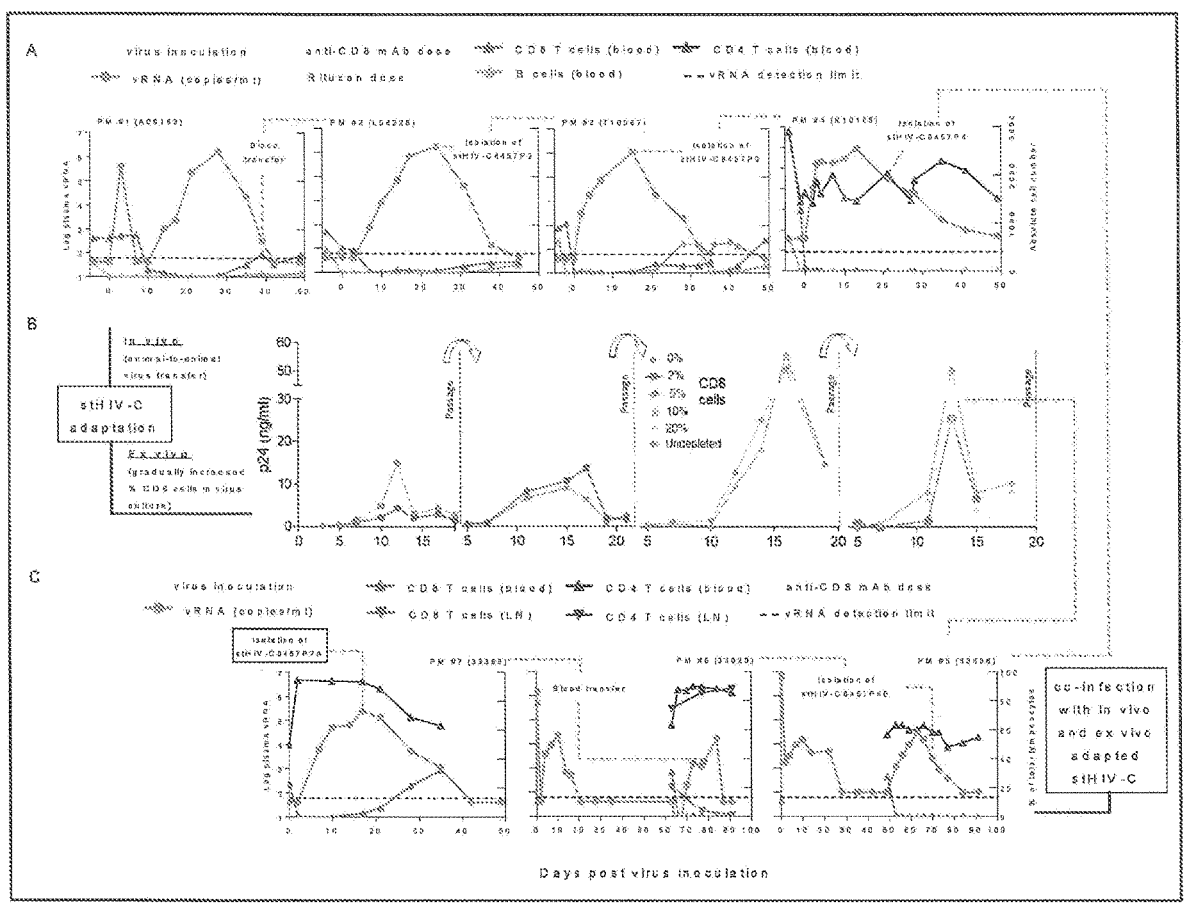
FIG. 4 is a graphical representation of the strategy employed to adapt the chimeric virus, stHIV-C8457, in the pig-tailed macaques, according to an exemplary embodiment.

Adaptation of stHIV8457 in Pig-Tailed Macaques: Restriction by the Innate Mechanisms As the stHIV8757 replicated in three out of six PM PBMCs but not in the cells of all randomly selected pig-tailed macaques, adaptation of this virus to the new species (PM, *Macaca nemestrina*) was required. For this adaptation, the successful strategy of unrestricted virus replication in an immunodepleted animal followed by selection in the immunocompetent host was used (as shown in FIG. 4).

In this adaptation series, four pig-tailed macaques were used. The animals were depleted of $CD8^+$ cells and B cells during the acute phase of stHIV-C8457 replication. In three out of four pig-tailed macaques, virus replication was controlled as the $CD8^+$ cells started becoming detectable in the blood. Whole blood (collected at the end of acute viremia) or virus isolated at peak viremia was inoculated in the next animal. The proviral DNA of stHIV-C8457 was inoculated into PM (#1, A09163) by intramuscular (i.m.) injection. The animal was depleted of B cells (by administration of rituximab, anti-CD20 mAb) (FIG. 4A) prior to virus inoculation, and $CD8^+$ cells were depleted by administration of the anti-CD8 mAb, cM-T807 immediately after virus inoculation. This animal showed vRNA copies in the blood immediately after DNA injection. However, viremia became undetectable within a short period of time but rebounded immediately after $CD8^+$ cells became undetectable in the circulation. Later, viremia was again controlled concomitant with the emergence of $CD8^+$ cells in the blood. Whole blood of the infected animal was transferred to the next immunodepleted PM (#2, L08228). In this animal, virus replication persisted for a short duration and control of viremia was again associated with the emergence of $CD8^+$ cells. Virus isolated from PM #2 was inoculated into the next immunodepleted PM (#3, T1 0067), which again showed that control of virus replication was associated with the emergence of $CD8^+$ cells. In next immunodepleted PM #4 (K 10 108), viremia persisted for a relatively longer period of time, which may have been due to the lack of reemerging $CD8^+$ cells. The data from these animals demonstrate a predominant role for $CD8^+$ cells in the control of viremia.

As in FIG. 4B (ex viva adaptation), stHIV-C8457 was passaged ex VIVO in the lymphocytes derived from a PM. To obtain progeny of stHIVC8457, which is relatively resistant to the inhibitory factors of CD8 cells, the percent of $CD8^+$ cells was increased gradually during successive ex vivo passages of virus. A defined number of autologous $CD8^+$ cells were added to the PBMC that were depleted of $CD8^+$ cells. This experiment yielded progeny virus that was able to grow better in the presence of $CD8^+$ cells. As in FIG. 4C (replication of adapted viruses in immunocompetent pig-tailed macaques), the in vivo adapted virus (stHIV-C8457P4, isolated from PM #4 (K10108)) and ex vivo adapted virus were co-inoculated into an immunocompetent PM (#5, 33388). The virus was able to replicate in this immunocompetent animal but only for short duration. When vRNA copies became undetectable in the blood, the animal was given a dose of anti-CD8 antibody. Immediately after $CD8^+$ cell depletion, the virus rebounded and a viremia level similar to peak viremia was observed. A viral reservoir was successfully established in this animal. Virus was reisolated (stHIV-C8457P5E) and then inoculated into a new immunocompetent PM (#6, 33029). Similar to the immunocompetent PM #5 (33388), virus replicated for a short duration but was able to establish a reservoir. After depletion of $CD8^+$ cells, the virus rebounded and whole blood was transferred into the next immunocompetent animal in the adaptation series (#7, 33389). Although CD8+ cells were not intentionally depleted in this recipient animal (#7, 33389), due to the presence of anti-CD8 antibodies in the donor blood, there was a transient decline in CD8+ cells. The animal showed viremia that was again immediately controlled concomitant with the emergence of CD8+ cells. StHIV-C8457P7A has been isolated from this last animal.

Figure 5:
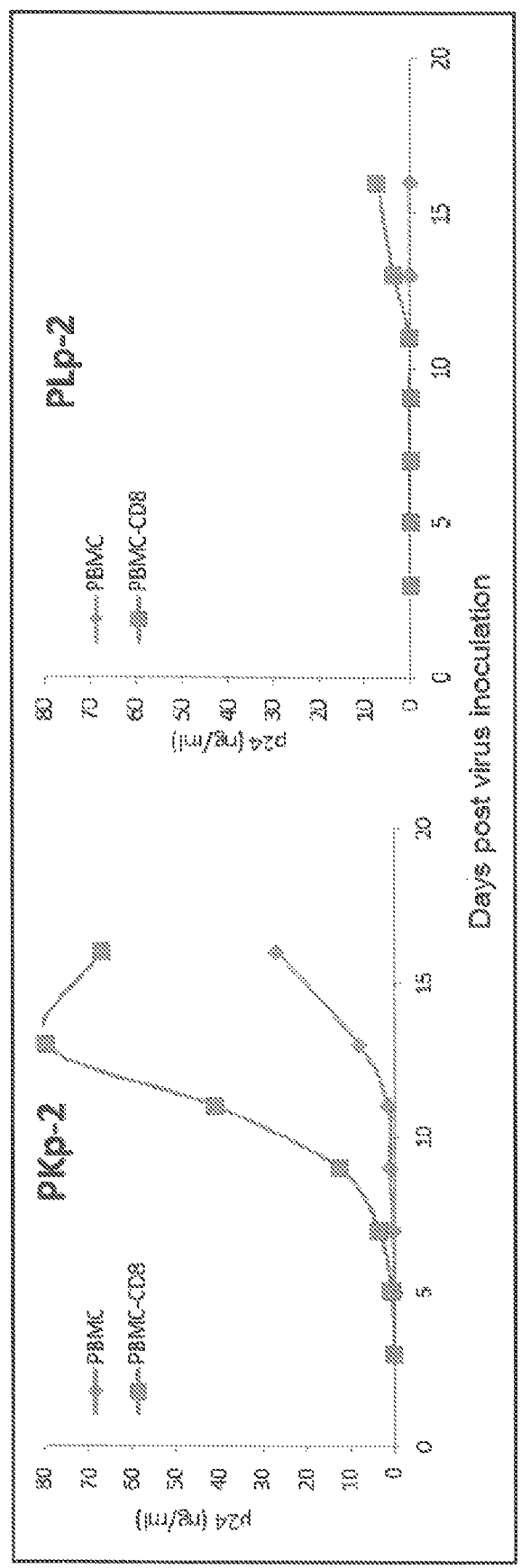
Figure 6:
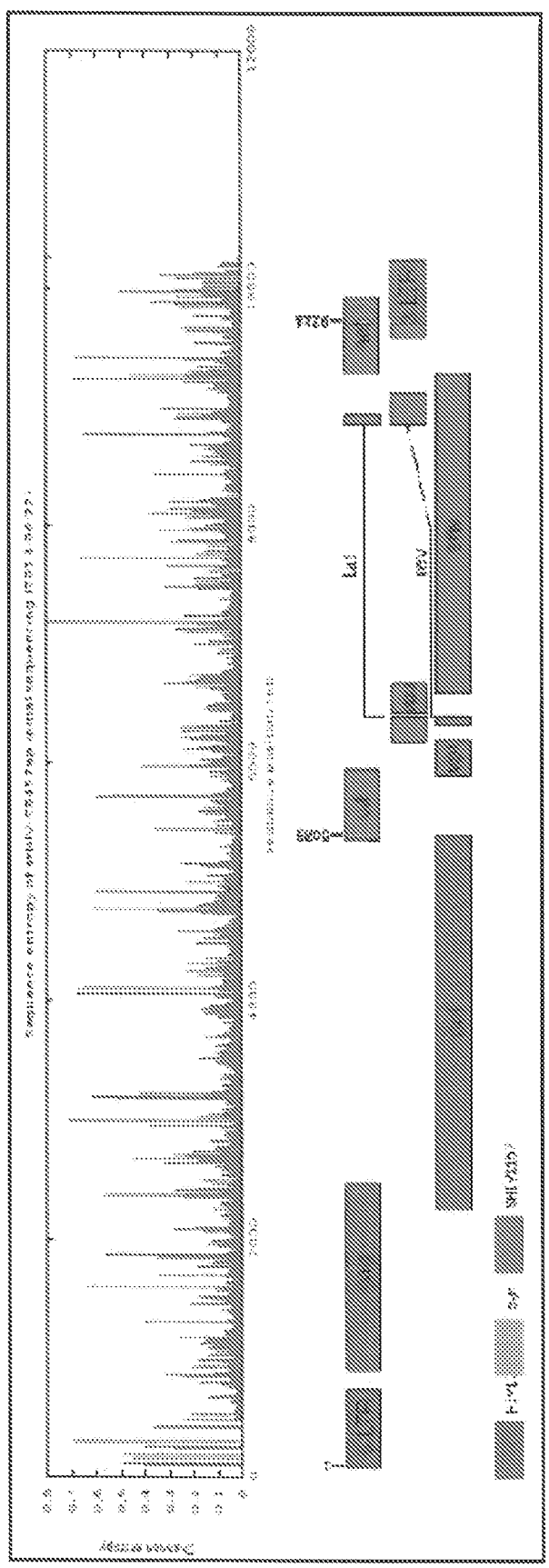

Experiments conducted to test the replication of stHIV-C8457 in vitro showed that virus yield was markedly higher in PBMC cultures depleted of CD8+ cells, as shown in FIG. 5. As these PBMC were derived from naive pig-tailed macaques, virus-specific cytolytic cells are unlikely to be present in the culture, and the control of virus replication can be ascribed to the virus inhibitory soluble factors produced by the CD8+ cells (innate mechanism(s)). Therefore, progeny of stHIV-C8457 that is resistant to CD8+ cell-produced, soluble, virus inhibitory factors was selected (FIG. 4B). In this experiment, the level of autologous CD8+ cells was gradually increased during virus passages in order to obtain progeny that is more resistant to CD8+ cell-mediated innate inhibition. This strategy was successful to obtain relatively more CD8+ cell-resistant virus through ex vivo adaptation (FIG. 4B). The ex vivo adapted virus was analyzed by deep genome sequencing (Illumina technology (Malboeuf et al., 2013)) in collaboration with Dr. Fischer, Los Alamos National Laboratory, Los Alamos. Data showed the emergence of variants during ex vivo adaptation (FIG. 6); further analysis is ongoing.

To select the virus with improved fitness, the in vivo adapted virus generated in immunodepleted pig-tailed macaques as well as ex vivo adapted virus were co-inoculated into three naive, immunocompetent pig-tailed macaques serially (FIG. 4C). Although virus replicated in all animals, viremia was rapidly controlled and steady-state virus replication was not obtained, a result that is similar to earlier data obtained during the adaptation of SHIV-A, SHIV-B, or SHIV-E. However, the virus was able to establish reservoirs in immunocompetent pig-tailed macaques. This was shown by the fact that virus immediately rebounded after depletion of CD8+ cells from PM #5 (33388) as well as PM #6 (33029). The last recipient animal of this adaptation series (PM #7, 33389) received the anti-CD8 antibodies that were present in the donor blood transferred from PM #6 (33029). This animal showed viremia for a longer period of time compared to pig-tailed macaques #5 and #6. Again, the viremia declined after the emergence of CD8+ cells in the blood.

One of the chimeric viruses was the isolated virus (stHIV-C8457P7A) from this animal using PBMC co-culture methods. When this virus was tested in the CEMx174.GFP cell-based assay to determine the X4 co-receptor usage, the results were negative, indicating lack of co-receptor switch during this adaptation process. This result is expected as HIV-C viruses (unlike HIV-B viruses) rarely show co-receptor switch. This ex vivo adapted stHIV-C8457, which had gained higher resistance to CD8 cell-mediated inhibition, as well as the in vivo adapted virus were further used in the innovative method to optimize sustained replication in the naive animals.

Development of the Animal Model

Many studies have shown that HIV-1 infection in humans and SIV infection in macaques lead to the induction of high levels of interferon IFN-α. The production of type 1 IFN (IFN-α, β, ω, κ, ε) is an early host response to different infectious agents that lead to the induction of a large number of LEN-stimulated genes (ISGs). Induction of ISGs inhibits the replication of many viruses. Recently, it has been shown that HIV-1 and SIV can replicate in the lymphocytes of their usual host even if ISGs were induced by IFN-α. In contrast, replication of HIV-1 and SIV was hypersensitive to IFN-α treatment in lymphocytes from unnatural hosts even when the viruses were engineered to overcome known restriction factors. IFN-α is known to induce high levels of tetherin that blocks release of virions from the surface of infected cells and myxovirus resistance 2 (MX2), which is a potent post-entry inhibitor of HIV-1 infection.

All type 1 IFNs bind the two common cell surface receptor components, IFNAR1 and IFNAR2 followed by activation of the intracellular JAK (Janus kinase)/STAT (signal transducers and activators of transcription) pathway. These signaling cascades lead to induction of ISGs. IFN type 1 receptor antagonist (IFN-1ant) can manipulate IFN-1 signaling in rhesus macaques. In a recently reported study (Sandler et al., 2014), IFN-1ant was given to macaques during first four weeks of SIV infection. Blocking of IFN-1 signaling resulted in delayed and decreased antiviral gene expression in PBMC and lymph nodes. The IFN-1ant recipient animals (n=6) had significantly higher plasma viral loads and SIN/RNA+ cells in lymph nodes than placebo macaques (n=9) during acute as well as chronic phase of infection. All IFN-1 ant recipient animals developed AIDS defining conditions in eight months after virus inoculation. In contrast, none of the placebo animal showed AIDS defining condition. The data suggests that IFN-1 signaling early in SIV infection is critical for innate immune control of virus replication. Blocking of this signaling mechanism during acute phase, results in significantly decreased virus control and rapid disease progression.

In development of the animal model herein, this novel IFN type 1 receptor antagonist (IFN-1ant) along with CD8+ cell depletion was used to facilitate stHIV-C8457 replication in the pig-tailed macaques. Due to administration of IFN-1ant, the signaling cascade induced by type 1 IFNs (which lead to induction of 'innate antiviral' state) is downregulated. Due to the depletion of CD8+ cells, innate viral inhibitory mechanisms of CD8+ are minimized. This would lead to minimization of impact of innate host immune mechanisms on the control of virus replication. This strategy will increase peak viremia and will also produce steady state virus replication.

Enhanced virus replication and high mutation and recombination rates of HIV-1 will lead to the emergence of swarms of mutants (viral quasispecies). These viral quasispecies are subject to selection pressure of antiviral mechanisms by inoculating them into naive immunocompetent host (pig-tailed macaques). Due to the inherent plasticity of many HIV-1 proteins, the viral variant with better replication fitness in the environment of new host species (the pigtailed macaque) is selected. The 'naturally selected' stHIV-C progeny that has adapted to replicate in the new host is evaluated for virus replication in two naive pig-tailed macaques and in the PBMC obtained from several immunocompetent pig-tailed macaques. After depletion of CD8+ cells from the pig-tailed macaques that carry reservoirs of stHIV-C8457, the virus will rebound and will be measurable in the plasma. Virus isolation is performed by the PBMC co-culture method in which mitogen-stimulated PBMC of an infected animal is co-cultured with mitogen-stimulated PBMC of a naive animal in the presence of exogenously added human interleukin (IL)-2. The culture supernatant is harvested every two days, and concentration of viral p24 protein is measured. The harvest with high p24 protein concentration is tested for $TCID_{50}$ by in the TZM-bl cell-based assay. Infectious virus stock is expanded in PBMC of naive pig-tailed macaques (without $CD8^+$ cell depletion) The virus stock is characterized for co-receptor usage by using a panel of cell lines that express HIV-1 receptor (CD4) and either one of the various coreceptors (CCR1, CCR2, CCR3, CCR5, CXCR4, Bob, Bonzo). These cells are exposed to the chimeric virus and virus replication is be monitored by measuring viral p24 protein concentration. For monitoring of $CD8^+$ cell level in the blood after administration of anti-CD8 antibodies, blood samples are sequentially collected. Cells are stained with anti-CD45, CD3, CD4, and CD8 antibodies. As anti-CD8 antibody (M-T807R1) can cross-block some anti-CD8 antibodies used for immunophenotyping, the antibody panel recommended by the NIH Nonhuman Primate Reagent Resource is used. The absolute number of $CD8^+$ cells is determined by performing complete blood count (CBC).

Figure 7:
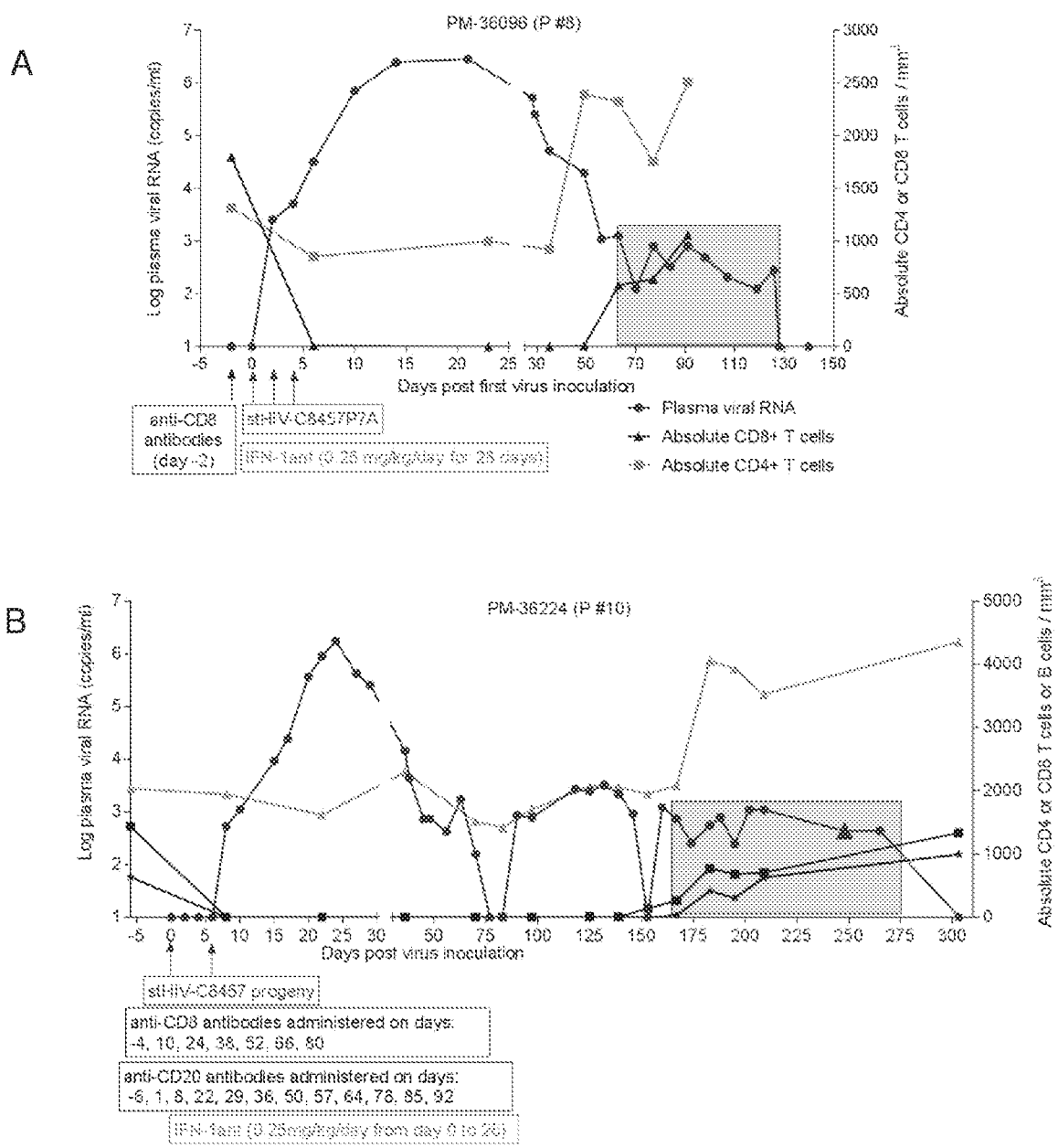

As shown in FIGS. 4A and 4C, in multiple pig-tailed macaques that viremia starts declining immediately after emergence of $CD8^+$ cells in the circulation. In the animals treated with IFN-1 antagonist, plasma viremia was sustained for longer periods of time. In a specific experiment, viremia was maintained in an animal for almost two months as shown below by the persistent viral RNA loads in FIGS. 7A and 7B. Replication of stHIV-C8457 was evaluated in two pig-tailed macaques for extended periods of time and even in the presence of CD8+ T cells. The virus was inoculated into an immunodepleted animal to facilitate virus replication. FIG. 7A shows the virus level in blood of PM 36096 (P #8). The virus level was measurable for more than three months. Interestingly, virus replication persisted for about two months even after the reemergence of CD8+ T cells in the blood (gray box). FIG. 7B shows the virus level in blood of PM 36224 (P #10). The virus level in the blood was measurable for more than eight months. Interestingly, virus replication persisted for about three months even after the reemergence of CD8+ T cells in the blood (gray box).

Viral replication for such a long period of time facilitates the emergence of new variant viruses that are better adapted for PMs, the new host species. PMs can be further subject to depletion of B cells (with the anti-CD20 mAb Rituxan) along with administration of IFN-1ant as well as depletion of $CD8^+$ cells with a cytotoxic mAb, which depletes both T cells and NK cells bearing the CD8 surface marker, to further facilitate virus replication. Thus, a robust unique animal model for evaluation of HIV vaccines and therapeutic modalities has been developed using the chimeric stHIV-c with robust replication in PMs.

Those skilled in the art will recognize, or be able to ascertain using no more than routine experimentation, many equivalents to the specific embodiments of the invention described herein. Such equivalents are intended to be encompassed by the following claims.

The invention claimed is:

1. A method for developing a human immunodeficiency virus (HIV) infection in a non-human primate, said method comprising: providing a ricin-human primate with weakened immune response, the weakened immune response being result of administration of IFN type 1 receptor antagonist to the non-human primate; and exposing the non-human primate to a chimeric HIV composition comprising a nucleotide sequence of SEQ ID NO: 1.

2. The method of claim 1, wherein the non-human primate is a pig-tailed macaque.

3. The method of claim 1, further wherein the weakened immune response is result of depletion of CD8+ cells in the non-human primate.

4. The method of claim 3, further wherein the weakened immune response is result of depletion of B cells in the non-human primate.

5. The method of claim 1, wherein the chimeric HIV composition further contains nucleotide sequences from the HIV1084i and SIVmac239 vif constructs.

6. A method for evaluating an anti-HIV compound in a non-human primate, said method comprising: providing a non-human primate with weakened immune response, the weakened immune response being result of administration of IFN type 1 receptor antagonist to the non-human primate; exposing the non-human primate to a chimeric HIV composition comprising a nucleotide sequence of SEQ ID NO: 1; administering an anti-HIV compound to the exposed non-human primate; and monitoring the exposed non-human primate for changes in immune cells of the exposed non-human primate in response to the anti-HIV compound.

7. The method of claim 6, wherein the non-human primate is a pig-tailed macaque.

8. The method of claim 6, wherein the chimeric HIV composition further contains nucleotide sequences from the HIV1084i and SIVmac239 vif constructs.

9. A method for evaluating a HIV vaccine in a non-human primate, said method comprising: providing a non-human primate with weakened immune response, the weakened immune response being result of administration of IFN type 1 receptor antagonist to the non-human primate; exposing the non-human primate to a chimeric HIV composition comprising a nucleotide sequence of SEQ ID NO: 1; administering a HIV vaccine to the exposed non-human primate; and monitoring the exposed non-human primate for changes in immune cells of the exposed non-human primate in response to the vaccine.

10. The method of claim 9, wherein the non-human primate is a pig-tailed macaque.

11. The method of claim 9, wherein the chimeric HIV composition further contains nucleotide sequences from the HIV1084i and SIVmac239 vif constructs.

* * * * *

```
                        SEQUENCE LISTING

<160> NUMBER OF SEQ ID NOS: 1

<210> SEQ ID NO 1
<211> LENGTH: 10119
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
tggatgggtt aatttactcc aagaaaaggc aagacatcct tgatctgtgg atctatcaca      60
cacaaggctt cttccctgat tggcaaaact acacaccggg accaggggac agatatccac     120
tgacctttgg atggtgcttc aagctagtgc cagttgaccc aagagaagta gaagaagcca     180
ctgaaggaga gaacagctgt ttactacacc ctatgagcct gcatggactg gaagatgcgg     240
acagagaagt attaaggtgg aagtttgaca gtcacctagc acacagacac ctggcccgcg     300
agctacatcc ggagttttac aaagactgct gacacagaag ggactttccg ctgggacttt     360
ccactggggc gttccaggag gtgtggtctg ggcgggactg gggagtggcc agccctcaga     420
tgctgcatat aagcagctgc ttttcgcttg tactgggtct ctctaggtag accagatctg     480
agcccgggag ctctctggct atctagggaa cccactgctt aagcctcaat aaagcttgcc     540
ttgagtgctc taagtagtgt gtgcccgtct gttgtgtgac tctggtaact agagatccct     600
cagacccgtt gtggtagtgt ggaaaatctc tagcagtggc gcccgaacag ggacttgaaa     660
gcgaaagtaa gaccagagga gatctctcga cgcaggactc ggcttgctga agtgcactcg     720
gcaagaggcg agagcggcgg ctggtgagta cgccaaattt tatttgacta gcggaggcta     780
ggaggagaga gatgggtgcg agagcgtcaa tattaagagg ggaaaaatta gataagtggg     840
aaaaaattag gttaaggcca gggggaaaga aacattatat gctaaaacac ttagtatggg     900
caagcaggga gctggaaaga tttgcactta accctggcct tttagagaca tcagaaggct     960
```

```
gtaaacaaat aatgaaacag ctacaaccag ctcttcagac aggaacagag gaacttagat   1020
cattatataa cacagtagca actctctgtt gtgtacatga aaagatagag gtacgagaca   1080
ccaaggaagc cttagacaaa atggaagaag aacaaaacaa aagtcagcaa aaaacacagc   1140
aagcagaagc ggctgacaaa ggaaaggtca gtcaaaacta tcctatagtg cagaatctcc   1200
aagggcaaat ggtacaccag gccatatcac cgagaactct gaatgcatgg gtaaaagtaa   1260
tagaggagaa ggctttcagc ccagaggtaa tacccatgtt tacagcatta tcagaaggag   1320 ccacccccaca agatttaaac accatgttaa atacagtggg gggacatcaa gcagccatgc   1380
aaatgttaaa agataccatt aatgaggagg ctgcagaatg ggataggtta catccagtgc   1440
atgcagggcc tattgcacca ggccaaataa gagaaccaag gggaagtgac atagcaggaa   1500
ctactagtac ccttcaggag caaatagcat ggatgacaaa taacccacct attccagtag   1560
gagacatcta taaaagatgg ataattctgg ggttaaataa aatagtaaga atgtatagcc   1620
ctgtcagcat tttggacata aaacaaggac caaaagaacc ctttagagac tatgtagaca   1680
ggttctttaa aactttaaga gctgaacagt ctacacaaga ggtaaaaaac tggatgacag   1740
acaccttgtt ggtccaaaat gcgaacccag attgtaagac catttttaaga gcattaggaa   1800 caggggctac attagaagag atgatgacag catgtcaggg agtgggggga cctagccaca   1860
aagcaagagt tttggctgag gcaatgagcc aagcaggcaa tacaaatata atgatgcaga   1920
gaagcaattt taaaggccct agaagaatta ttaaatgttt caactgtggc aaggagggc    1980 acatagctag aaattgcagg gcccccagga aaaaggctg ttggaaatgt ggaaaggaag    2040
gacaccaaat aaaagattgt actgagaggc aggctaattt tttagggaaa atttggcctt   2100
cccacaaggg aaggccaggg aatttccttc agaacagacc agagccaaca gccccaccag   2160
cagagagttt caggttcgag gagacaaccc ccgctccgaa gcaggagccg aacgacaggg   2220
aacccttaac ttccctcaaa tcactctttg gcagcgaccc ctcgtctcaa taaaagtagg   2280
gggccaaata agggaggctc tcttagatac aggagcagat gatacagtat tagaagacat   2340
aaatttgcca ggaaaatgga accaaaaat gataggagga attggaggtt ttatcaaagt    2400
aagacagtat gaacaaatac ttatagaaat ttgtggaaaa aaggctatag gtacagtatt   2460
agtaggacct accccctgtca acataattgg aaggaatatg ttgacacagc ttgggtgtac   2520
actaaatttt ccaattagtc ccattgaaac tgtaccagta aaattaaagc cagggatgga   2580
tggcccaagg gttaaacaat ggccattgac agaagagaaa ataaaagcat taacagcaat   2640
ttgtgaagac atggagaagg aaggaaaaat tacaaaaatt gggcctgaaa atccatataa   2700
cactccagta tttgccataa aaaagaagga cagtactaag tggagaaaat tagtagattt   2760
cagggaactc aataaaagaa ctcaagactt tgggaagtt caattaggaa taccacaccc    2820
agcagggtta aaaaagaaaa aatcagtgac agtgctggat gtgggggatg catatttttc    2880
agttccttta gatgaaaact tcaggaaata tactgcattc accataccta gtataaacaa   2940
tgcagcacca gggattagat atcaatataa tgtgcttcca cagggatgga aaggatcacc   3000
agcaatattc cagagtagca tgacaaaaat cttagagccc tttaggacac aaaatccaga   3060
catagttatc tatcaatata tggatgactt gtatgtagga tctgacttgg aaatagggca   3120
acatagagca aaaatagaga gttaagagaa acatttattg aaatggggac tcaccacacc   3180
agacaagaaa catcagaaag aaccccccatt tctttggatg gggtatgaac tccatcctga   3240
caaatggaca gtacagccta tacagctgcc agaaaaggat agctggactg tcaatgatat   3300
```

```
acagaagtta gtgggaaaat taaactgggc aagtcagatt tacccaggga ttaaagtaaa      3360
gcaactgtgt aaactcctta ggggagccaa agcattaaca gacatagtac cactgactga      3420
agaagcagaa ttagaattgg cagaaaacag ggaaatttta aaagaaccag tacatggagt      3480
atattatgac ccatcaaaag acttaatagc tgaaatacag aaacagggt atggccaatg       3540 gacataccaa atttaccaag aaccattcaa aaatctgaaa acagggaagt atgcaaaaat     3600
gaggactgcc cacactaatg atgtaaaaca gttaacagag gcagtgcaaa aaatagccct     3660
ggaaagcata gtaatatggg gaaagactcc taaatttaga ctacccatcc aaaaagacac     3720
atgggaggca tggtggacag aatattggca agccacctgg attcctgaat gggagtttgt     3780
taatacccct cctctagtaa aattatggta ccagctggag aaagaaccaa taataggagc     3840
agaaactttc tatgtagatg gagcagctaa tagggaaact aaagcaggaa aggcagggta     3900
tgttactgac aaaggaaggc agaaaatcgt ttctctaact gaaacaacaa atcagaaggc     3960
tgaactacaa gcagttcagc tagctttgca ggattcagga ttagaagtaa acatagtaac     4020
agactcacag tatgccttag gaattattca agcacaacca gataagagtg aatcagaatt     4080
agtcgctcag ataatagagc agttaataaa aaaggaaagg gtctacctgt catgggtacc     4140
agcacataaa ggaattggag gaaatgaaca agtagataaa ttagtcagca gtggaataag     4200
gaaagtgctg tttctagatg gaatagataa ggctcaagaa gaccatgaaa aatatcacag     4260
caattggaga gcaatggcta atgagtttaa tctgccaccc atagtagcaa aagaaatagt     4320
agctagctgt gataaatgtc aactaaaagg ggaagccata catggacaag tagactgtag     4380
tccagggatc tggcaattag attgtacaca tttagaagga aaaatcatcc tggtagcagt     4440
ccatgtagcc agtggctaca tagaagcaga ggttatccca gcagaaacag gacaagaaac     4500
agcatactac atactaaaat tagcaggaag atggccagta aagtaatac atacagataa     4560 tggcagtaat ttcaccagtg ctgcagttaa ggcagcctgt tggtgggcag gtatccaaca     4620
ggaatttgga atcccctaca atccccaaag tcagggagta gtagaatcca tgaataaaga     4680
attaaagaaa atcatagggc aggtaagaga tcaagctgag caccttaaga cagcagtaca     4740
aatggcagta ttcattcaca atttaaaag aaaaggggggg attggggggt acagtgcagg     4800
ggagagaata atagacataa tagcaacaga catacaaact aaagaattac aaaaccaaat     4860
tttaaaaatt cgaaattttc gggtttatta cagagacagc agagaccct tttggaaagg     4920 accagccaaa ctactctgga aaggtgaagg ggcagtagta atacaagata atagtgacat     4980
aaaggtagta ccaaggagga aagtaaaaat cattaaggac tacggaaaac agatggcagg     5040
tgctgattgt gtggcaggta gacaggacga ggattagacc gcggttatgg aggaggaaaa     5100
gaggtggata gcagttccca catggaggat accggagagg ctagagaggt ggcatagcct     5160
cataaaatat ctgaaatata aaactaaaga tctacaaaag gtttgctatg tgccccattt     5220
taaggtcgga tgggcatggt ggacctgcag cagagtaatc ttcccactac aggaaggaag     5280
ccatttagaa gtacaagggt attggcattt gacaccagaa aaagggtggc tcagtactta     5340
tgcagtgagg ataacctggt actcaaagaa cttttggaca gatgtaacac caaactatgc     5400
agacatttta ctgcatagca cttatttccc ttgctttaca gcgggagaag tgagaagggc     5460
catcagggga gaacaactgc tgtcttgctg caggttcccg agagctcata agtaccaggt     5520
accaagccta cagtacttag cactgaaagt agtaagcgat gtcagatccc agggagagaa     5580
tcccacctgg aaacagtgga gaagagacaa taggagaggc cttcgaatgg ctaaacagaa     5640
cagtagagga gataaacaga gaggcggtaa accacctacc aagggagcta attttccagg     5700
```

```
tttggcaaag gtcttgggaa tactggcatg atgaacaagg gatgtcacca agctatgtaa   5760
aatacagata cttgtgttta atacaaaagg ctttatttat gcattgcaag aaaggctgta   5820
gatgtctagg ggaaggacat ggggcagggg gatggagacc aggacctcct cctcctcccc   5880
ctccaggact agcataaatg gaagaaagac ctccagaaaa tgaaggacca caagggaac   5940 catgggatga atgggtagtg gaggttctgg aagaactgaa agaagaagct ttaaaacatt   6000
ttgatcctcg cttgctaact gcacttggta atcatatcta taatcgtcac ggagacactc   6060
tagagggagc aggagaactc attagaatcc tccaacgagc gctcttcatg catttcagag   6120
gcggatgcat ccactccaga atcggccaac ctggggagg aaatcctctc tcagctatac    6180
cgccctctag aagcatgcgc atgctgtaga gcaagaaatg gagccagtag atcctagact   6240
agagccctgg aagcatccag gaagcaggcc taaaactgct tgtaccaatt gctattgtaa   6300
aaagtgttgc tttcattgcc aagtttgttt cataacaaaa gccctaggca tctcctatgg   6360
caggaagaag cggagacagc gacgaagagc tcatcagaac agtcagactc atcaagcttc   6420
tctatcaaag cagtaagtag tacatgtaat gcaatctata caaatagaaa tagtagcatt   6480
agtagtagca ataataatag caatagttgt gtggtccata gtaatcatag aatataggaa   6540
aatattaaga caaagaaaaa tagacaggtt aattaataga ctaatagaaa gagcagaaga   6600
cagtggcaat gagagtgaag gagaaatatc agcacttgtg gagatggggg tggagatggg   6660
gcatcatgct ccttgggatg ttgatgatct gtagtgctac agaaaaattg tgggtcacag   6720
tctattatgg ggtacctgta tggaaagaag caaaaactac tttattctgt gcatcaaatg   6780
ctaaagcata tgagaaagaa gtacataaca tctgggctac acatgcctgt gtacccacag   6840
accccaaccc acaagaaata gttttgggaa atgtaacaga aaattttaac atgtggaaaa   6900
atgacatggt ggatcagatg catgaggata taatcagttt atgggatcaa agcctaaagc   6960
catgtgtaaa gttgacttca ctctgtgtca ctttaaagtg tagtaatttt accgggaaga   7020
gtaatgttac ctacaaaggg gatatggaag taaaaaattg ctctttcaat gtaaccacag   7080
aaataagaga taagaagcag aaagtgtatg ctctttttta tagacttgat ataacaccac   7140
ttgatgacaa ctctagtgag tatatattaa taaattgcaa ttcctcaacc ataacacaag   7200
cctgtccaaa ggtcaatttt gacccaattc ctatacatta ttgtgctcca gctggttatg   7260
cgattctaaa gtgtaataat aagacattta atgggacagg accatgccat aatgtcagta   7320
cagtacaatg tacacatgga attaagccag tggtatcaac tcaactactg ttaaacggta   7380
gcctagcaga agggagata ataattagat ctgaaaatct gacagacaat gtcaaaacaa    7440
taatagtaca ctttaatgaa tctgtagaaa ttacttgtac aagacccaac aataatacaa   7500
gaaaaagtat aagcatagga ccaggacaag caatctatgc cacaggtgat ataataggag   7560
acataagaca agcacactgt aacattagta agaaaattg gaacaaaact ttacaatggg    7620
taaggggaaa attaaaagaa cacttcccta ataaacaat agtatttaaa ccatcctcag     7680
gaggggatct agaaattaca acacatagct ttaattgtag aggagaattt ttctattgca   7740
acacatcaaa actgttaat agtacagaca atagtacaca catgggtaca gaaataata     7800 caatcatcac aatcccatgt agaataaaac aaattataaa catgtggcag gaggtaggac   7860
gagcaatgta tgcccccccc atagaaggaa acataacatg taaatcaaat atcacaggac   7920
tactactggt acgtgatgga ggatgggaca acagtacaaa tgacacagaa acattcaggc   7980
ctggaggagg agatatgagg gacaattgga gaagtgaatt atataaatat aaggtggtag   8040
```

```
aagtcaagcc attgggaata gcacccacta aggcaaaaag gagagtggtg gagagagaaa    8100
aaagagcagt gggaatagga gctgtgttcc ttgggttctt gggagcagca ggaagcacta    8160
tgggcgcggc gtcaataacg ctgacggtac aggccagaca actgttgtct ggtatagtgc    8220
agcagcaaga caatttgctg agagctatag aggcgcaaca acatatgttg caactcacag    8280
tctggggcat taagcagctc caggcgagag tcctggctat agaaagatac ctacaggatc    8340
aacagctcct agggatttgg ggctgctctg gaaaactcat ctgcaccact gctgtgcctt    8400
ggaacgacag ttggagtaat aaatctcaaa cagatatttg ggagaacatg acctggatgc    8460
agtgggatag agaaattagt agacacacag acacaatata caggttgctt gaagactcac    8520
aaaaccagca ggagaaaaat gaaaaagatt tattagcatt ggacagttgg aaaaatttgt    8580
ggaattggtt tagcataaca aggtggctgt ggtatataaa aatattcata atgatagtag    8640
gaggcctgat aggtttgaga ataattttg ctgtgctctc gatagtgaat agagttaggc     8700
agggatactc accattatcg tttcagaccc acctcccact tccgagggga gccgacaggc    8760
ccgaaggaat agaagaagaa ggtggagaga gagacagaga cagatccatt cgattagtga    8820
ccggatcctt agcacttatc tgggacgatc tgcggagcct gtgcctcttc agctaccacc    8880
gcttgagaga cttactcttg attgtaacga ggactgtgga actcctggga cgcagagggt    8940
gggaagccct caaatattgg tggaatctcc tactgtattg gagtcaggaa ctaaagaata    9000
gtgctgttag cttgctcaac gccacagcca tagcagtaag acaatacggg tggagctatt    9060
tccacgaggc ggtccaggcc gtctggagat ctgcgacaga gactcttgcg ggcgcgtggg    9120
gagacttatg ggagattctt aggagaggtg gaagatggat actcgcaatc cccaggagga    9180
ttagacaagg gctcgagctc actctcttgt gagcgatcgc atgggggca agtggtcaaa     9240 aagcagtata gttggatggc ctgctgtaag agaaagaata agacaaactg ctccagcagc    9300
aacaggagta ggagcagcgt ctcaagactt agatacacat ggggcactta caaccagcaa    9360
cacagttagc aacaatgctg attgtgcctg gttggaagca caagaggaga aagacgaggt    9420
aggctttcca gtcagacctc aggtaccttt aagaccaatg acttataagg cagcattcga    9480
tctcagcttc tttttaaaag aaaaggggg actggatggg ttaatttact ccaagaaaag     9540
gcaagacatc cttgatctgt ggatctatca cacacaaggc ttcttccctg attggcaaaa    9600
ctacacaccg ggaccagggg tcagatatcc actgacctt ggatggtgct tcaagctagt     9660
gccagttgac ccaagggaag tagaagaagc cactgaagga gagaacagct gtttactaca    9720
ccctatgagc ctgcatggac tggaagatgc ggacagagaa gtattaaggt ggaagtttga    9780
cagtcaccta gcgcacagac acatggcccg cgagctacat ccggagtttt acaaagactg    9840
ctgacacaga agggactttc cgctgggact ttccactggg gcgttccagg aggtgtggtc    9900
tgggcgggac tggggagtgg ccagccctca gatgctgcat ataagcagct gcttttcgct    9960
tgtactgggt ctctctaggt agaccagatc tgagcccggg agctctctgg ctatctaggg   10020
aacccactgc ttaagcctca ataaagcttg ccttgagtgc tctaagtagt gtgtgcccgt   10080
ctgttgtgtg actctggtaa ctagagatcc ctcagaccc                          10119
```